United States Patent [19]

Frölich et al.

[11] Patent Number: 5,464,868
[45] Date of Patent: Nov. 7, 1995

[54] PROSTAGLANDIN E1 DERIVATIVES FOR TRANSDERMAL ADMINISTRATION AND METHODS OF TREATMENT THEREWITH

[76] Inventors: Jürgen C. Frölich, Röhrichtweg 11, 3000 Hannover 71; Herbert Bippi, Warburghof 10B, 3000 Hannover 61, both of Germany

[21] Appl. No.: 44,511

[22] Filed: Apr. 7, 1993

Related U.S. Application Data

[62] Division of Ser. No. 483,995, Feb. 22, 1990, Pat. No. 5,219,885, which is a continuation of Ser. No. 156,177, Feb. 16, 1988, abandoned.

[30] Foreign Application Priority Data

Feb. 16, 1987 [DE] Germany .......................... 37 04 825.2

[51] Int. Cl.⁶ .................................................. A61K 31/557
[52] U.S. Cl. ................................................................ 514/530
[58] Field of Search ........................................... 514/530

OTHER PUBLICATIONS

Shirakwawa, Jpn. J. Anesthesiol 41/6 (1000–3) 1992.

Primary Examiner—Robert Gerstl
Attorney, Agent, or Firm—Kenyon & Kenyon

[57] ABSTRACT

The invention describes prostaglandin E1 derivatives as pharmacologically active agents, and pharmaceutical compositions containing these compounds, especially for transcutaneous administration.

2 Claims, 1 Drawing Sheet

PROSTAGLANDIN E1 DERIVATIVES FOR TRANSDERMAL ADMINISTRATION AND METHODS OF TREATMENT THEREWITH

The present application is a divisional application of Ser. No. 07/483,995, filed Feb. 22, 1990, now U.S. Pat. No. 5,2219,885, which is a continuation of Ser. No. 07/156,177 filed Feb. 16, 1988, and now abandoned.

BACKGROUND OF THE INVENTION

The invention relates to prostaglandin E1 derivatives (PGE1 derivatives) as pharmacologically active agents and to pharmaceutical compositions—especially for transcutaneous (transdermal) application—which contain a PGE1 derivative.

DE-A-27 53 986 and the corresponding U.S. Pat. No. 4,205,178 disclose 6-keto prostaglandin E1 derivatives, especially the 6-keto PGE1 methyl ester.

A number of biological and pharmacological effects are described for these compounds. Various routes of administration are indicated for the various kinds of illnesses to be treated, e.g. oral, intravenous, subcutaneous, intra-arterial, buccal, rectal and intra-vaginal administration. Topical administration is described in connection with skin injuries or skin diseases at or near the site of the injury or disease.

6-keto prostaglandin E1 derivatives are also described in DE-A-28 40 032, in which the authors also refer to various forms of pharmacological activity and administration.

Prostaglandin E1 (PGE1) and 6-keto prostaglandin E1 (6-k PGE1) can be used for the treatment of several diseases. These diseases include peripheral occlusive diseases, complications in arteriosclerosis such as Menière's disease or acute loss of hearing, acute myocardial infarctation, unstable angina pectoris, acute ischaemic strokes, impotence, bronchial asthma, impaired hair growth and rejection following kidney transplants; see H. Sinzinger and W. Rogatti, Prostaglandin E1 in atherosclerosis, Springer Verlag Berlin—Heidelberg—New York, 1986; S. Schrey, PGE1, Therapie der arteriellen Verschlußkrankheit, Universitätsdruckerei and Verlag Dr. C. Wolf und Sohn, Munich, 1985. PGE1 is used for the treatment of chronic arterial occlusive diseases in phase III and IV. This condition calls for intra-arterial or intravenous infusion which results in a severe limitation in the use of PGE1, as the infusion is not only a strain on the patient, but also involves a certain risk of arterial haemorrhage. Neither route of administration (i.a. and i.v.) is suitable for continuous therapy in ambulatory patient care. However, long-term administration would be most appropriate for these diseases. The oral adminstration of PGE1 is always problematic as either the very low bio-availability rules out such administration, or the typical undesired effects (nausea, vomiting, diarrhoea) are prohibitive due to the high concentration of the drug in the gastrointestinal tract when orally administered.

SUMMARY OF THE INVENTION

The object underlying the invention is to provide PGE1 and PGE1 derivatives as pharmaceutical compositions or pharmacologically -active agents. The PGE1 derivatives, which were especially developed as pharmacologically active agents for transcutaneous, transdermal adminstration, are absorbed by the skin and subsequently split by hydrolases into prostaglandin E1 or 6-keto PGE1 and alcohol. The PGE1 derivatives thus fulfill the requirements of the "Pro-Drug" Concept and avoid the disadvantages of PGE1 and 6-keto PGE1 when adminstered arterially, intravenously or orally.

The subject matter of the invention is therefore prostaglandin E1 derivatives of the general formula I

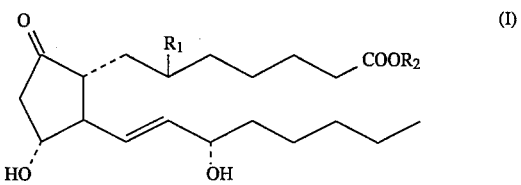

in which $R_1$ is a hydrogen atom and $R_2$ is a $C_{1-4}$ alkyl residue, as pharmacologically active agents.

A further subject matter of the invention is a pharmaceutical composition containing a prostaglandin E1 derivative according to formula I.

Still a further subject matter of the invention is the use of prostaglandin E1 derivatives of general formula I,

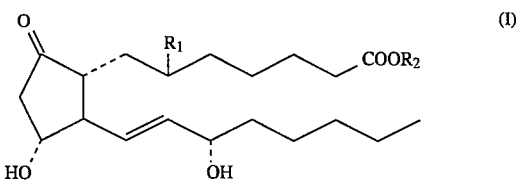

in which $R_1$ is a hydrogen atom (PGE1) or a carbonyl oxygen atom (6-k-PGE1) and $R_2$ is a $C_{1-4}$ alkyl residue for the preparation of a pharmaceutical composition to be administered transcutaneously.

DETAILED DESCRIPTION

Figure 1:
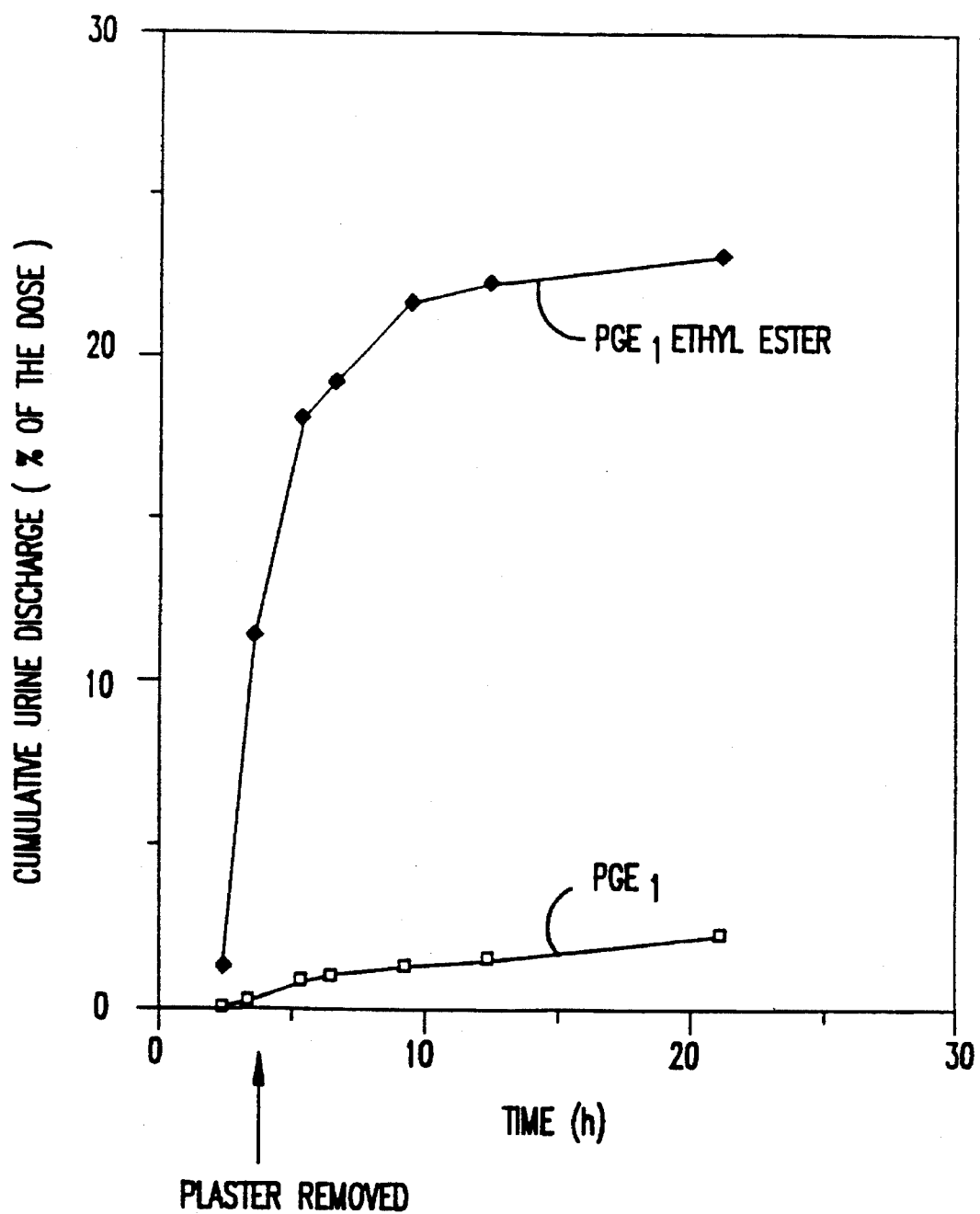
FIG. 1 shows the absorption rate of PGE1 and PGE1 ethyl ester which has been determined as the cumulative urinary excretion following transcutaneous administration.

Specific examples of alkyl residues are the methyl, ethyl, n-propyl, isopropyl, n-butyl, isobutyl and tertiary butyl group.

Due to the non-toxicity of the fragments, the preferred group $R_2$ is the ethyl group.

The preparation of the compounds of general formula I is carried out according to methods known per se via esterification of PGE1 and 6-k PGE1. The methyl and ethyl ester, for instance, are prepared by reacting the same with diazomethane or diazoethane; also see Ch. J. Sih et al., *J. Am. Chem. Soc.*, Vol. 97 (1975), pp. 857 to 865.

The compounds of general formula I can be used to treat circulatory insufficiencies, for instance of the brain, the heart and the extremities, to inhibit platelet aggregation (thrombocyte aggregation), impotence and to treat allergic reactions such as bronchial asthma, rejection following transplantations and impaired hair growth. Typical examples of deficiencies in the cerebral blood supply are transitory cerebral ischaemia, acute loss of hearing, vertigo caused by circulatory insufficiencies and ischaemic strokes. Typical examples of deficiencies in the myocardial blood supply are angina pectoris and myocardial infarction. Typical examples of deficiencies in the blood supply of the extremities are periphal arterial circulatory insufficiencies in arteriosclerosis and Raynaud's disease and Raynaud's syndrom.

The compounds of general formula I can also be used to treat gastrointestinal ulcers and ulcers of the skin. Typical examples of gastrointestinal ulcers are ulcus ventriculi, duodenal ulcers and ulcerative colitis (Crohn's disease). A typical example of a skin ulcer is ulcus cruris. The compounds of general formula I have a cyto-protective effect. The cells exhibit increased resistance to noxious stimuli.

The compounds of general formula I can further be used to treat haematomas, especially surface haematomas.

In addition to transcutaneous (transdermal) administration, the compounds of general formula I can also be administered by inhalation, intravenously and intra-arterially and in each case incorporated into microsomes.

The preparation of pharmaceutical compositions is carried out according to conventional methods. For the preparation of pharmaceutical compositions to be administered transcutaneously, the compounds of general formula I can be mixed with a gel, ointment or liquid vehicle either with or without various solvents and stabilizers. The packages used are sprays, tubes, ampules and individual doses. Once applied to the skin either with or without an additional occlusive dressing, the active agent is absorbed.

The compounds of general formula I can also be placed either with or without stabilizers and solvents onto a plaster and can then be applied as such.

The conversion of the ethyl ester to PGE1 in the human body was demonstrated in the following way: an isotopically labelled PGE1 ethyl ester was applied in the manner described above. The isotopically labelled urinary metabolites were separated with HPLC and compared with the retention time of the main metabolite of PGE1 (7α-hydroxy-5,11-diketotetranorosta- 1,20-dioic acid). It was found that after administration of the PGE1 ethyl ester, the main metabolite was identical to the main metabolite after administration of PGE1. This proves that the PGE1 ethyl ester is a pro-drug of PGE1.

The following examples illustrate the invention.

EXAMPLE 1

The preparation of prostaglandin E1 ethylester.

Excess diazoethane in diethyl ether (17 mg/ml; 0.3 mmol) is added to 500 μg PGE1 (1.31 μmol) in 500 μl ethanol under stirring and cooling. The reaction mixture is taken out of the cooler and is stirred until it reaches room temperature. Stirring is then continued for a further 30 minutes. The excess diazoethane and the ethanol are removed at room temperature by a stream of nitrogen. The product is purified by high-pressure liquid chromatography (RP 18).

In the same manner and with excess diazoethane, 500 μg of 6-keto PGE1 in 500 μl of ethanol are reacted and processed in diethyl ether. The ester is purified by high-pressure liquid chromatography (RP 18).

EXAMPLE 2

250 μg of prostaglandin E1 ethyl ester together with an isotopically labelled PGE1-ethyl-ester in 250 μl of ethanol were worked into 2 g of a gel vehicle of the composition as indicated below. The gel was applied to the upper arm and rubbed in for 1 minute. The application area was covered with a plastic foil.

One week later, 250 μg of prostaglandin E1 together with an isotopically labelled PGE1 in 250 μl of ethanol were mixed with 2 g of a gel vehicle of the composition as indicated below. It, too, was applied to the upper arm and rubbed in for 1 minute.

Measurement of the absorbed quantity was carried out by determining the isotopically labelled prostaglandin metabolites in the urine. For this, the total urine was collected in portions from the beginning of the application onwards. Four hours after the application, the plastic film was removed and the excess gel wiped off. As can be seen in FIG. 1, the absorption rate of PGE1 ethyl ester (23 %) was clearly better than that of PGE1 (approx. 4 %).

The gel vehicle was prepared according to the following recipe:

| | |
|---|---|
| Isopropanol | 40.0 g |
| Diisopropyl adipate | 0.5 g |
| Carbopol 940 | 2.0 g |
| Trometamol | 1.91 g |
| Purified water | ad 100.0 g |

The isopropanol can also be exchanged for ethanol.

The water, alcohol and diisopropyl adipate are mixed, the carbopol is dispersed in this mixture and left to swell. The gel is neutralized with the aqueous trometamol-solution.

What is claimed is:

1. A method for treatment of ulcer of the skin in a patient comprising the step of contacting the skin of said patient with a transdermal pharmaceutical composition in a transdermally effective amount, said pharmaceutical composition itself comprising a $C_{1-4}$ alkyl ester of prostaglandin E1 or 6-keto prostaglandin E1.

2. A method according to claim 1 wherein the pharmaceutical composition used therein further comprises a transdermally effective carrier selected from the group of substances consisting of gels, ointments, or liquid vehicles and, optionally, additional solvent or stabilizer.

* * * * *